US007725150B2

(12) United States Patent
Tupin, Jr. et al.

(10) Patent No.: US 7,725,150 B2
(45) Date of Patent: May 25, 2010

(54) SYSTEM AND METHOD FOR EXTRACTING PHYSIOLOGICAL DATA USING ULTRA-WIDEBAND RADAR AND IMPROVED SIGNAL PROCESSING TECHNIQUES

(75) Inventors: Joe Paul Tupin, Jr., Loomis, CA (US); Robert Martinez Van Rooyen, Antelope, CA (US); Richard Jensen Rollins, Penryn, CA (US)

(73) Assignee: LifeWave, Inc., Los Altos, CA (US)

( * ) Notice: Subject to any disclaimer, the term of this patent is extended or adjusted under 35 U.S.C. 154(b) by 2031 days.

(21) Appl. No.: 10/456,290

(22) Filed: Jun. 4, 2003

(65) Prior Publication Data
US 2004/0249258 A1    Dec. 9, 2004

(51) Int. Cl.
*A61B 5/05* (2006.01)
(52) U.S. Cl. .................. 600/407; 600/430; 600/481; 382/128
(58) Field of Classification Search ................ 600/407, 600/430; 382/128
See application file for complete search history.

(56) References Cited

U.S. PATENT DOCUMENTS

| 5,292,348 | A | * | 3/1994 | Saumarez et al. ............ 607/5 |
| 5,345,471 | A | | 9/1994 | McEwan |
| 5,361,070 | A | | 11/1994 | McEwan |
| 5,457,394 | A | | 10/1995 | McEwan |
| 5,465,094 | A | | 11/1995 | McEwan |
| 5,510,800 | A | | 4/1996 | McEwan |
| 5,512,834 | A | | 4/1996 | McEwan |
| 5,517,198 | A | | 5/1996 | McEwan |
| 5,519,400 | A | | 5/1996 | McEwan |
| 5,521,600 | A | | 5/1996 | McEwan |
| 5,523,760 | A | | 6/1996 | McEwan |
| 5,563,605 | A | | 10/1996 | McEwan |
| 5,573,012 | A | | 11/1996 | McEwan |
| 5,576,627 | A | | 11/1996 | McEwan |
| 5,581,256 | A | | 12/1996 | McEwan |
| 5,589,838 | A | | 12/1996 | McEwan |
| 5,609,059 | A | | 3/1997 | McEwan |
| 5,610,611 | A | | 3/1997 | McEwan |
| 5,630,216 | A | | 5/1997 | McEwan |
| 5,661,385 | A | | 8/1997 | McEwan |
| 5,682,164 | A | | 10/1997 | McEwan |
| 5,736,958 | A | * | 4/1998 | Turpin ...................... 342/179 |
| 5,754,144 | A | | 5/1998 | McEwan |
| 5,757,320 | A | | 5/1998 | McEwan |
| 5,766,208 | A | | 6/1998 | McEwan |

(Continued)

OTHER PUBLICATIONS

PCT International Preliminary Report on Patentability mailed on Dec. 22, 2005 regarding PCT/US2004/016820 filed on May 28, 2004, including Written Opinion of the International Searching Authority (7 pgs.).

*Primary Examiner*—Brian Casler
*Assistant Examiner*—James Kish
(74) *Attorney, Agent, or Firm*—Shay Glenn LLP

(57) ABSTRACT

Disclosed is a variant of ultra-wide band (UWB) radar known as micropower impulse radar (MIR) combined with advanced signal processing techniques to provide a new type of medical imaging technology including frequency spectrum analysis and modern statistical filtering techniques to search for, acquire, track, or interrogate physiological data. Range gate settings are controlled to depths of interest within a patient and those settings are dynamically adjusted to optimize the physiological signals desired.

51 Claims, 14 Drawing Sheets

U.S. PATENT DOCUMENTS

| | | |
|---|---|---|
| 5,767,953 A | 6/1998 | McEwan |
| 5,774,091 A | 6/1998 | McEwan |
| 5,832,772 A | 11/1998 | McEwan |
| 5,883,591 A | 3/1999 | McEwan |
| 6,213,947 B1 * | 4/2001 | Phillips ..................... 600/443 |
| 6,233,479 B1 * | 5/2001 | Haddad et al. .............. 600/430 |
| 6,292,433 B1 * | 9/2001 | Gilbert et al. ............... 367/138 |
| 2003/0088180 A1 * | 5/2003 | Van Veen et al. ............ 600/430 |

* cited by examiner

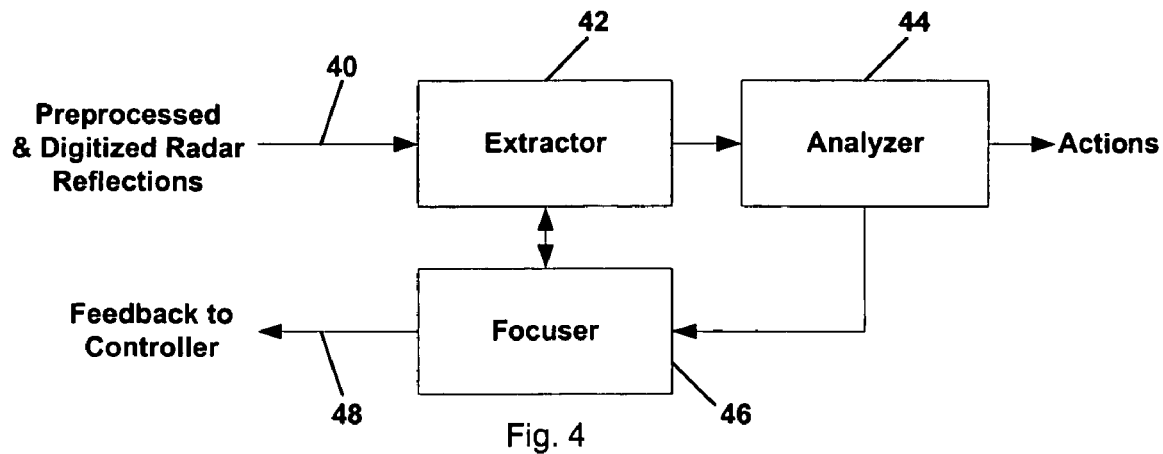
Fig. 4
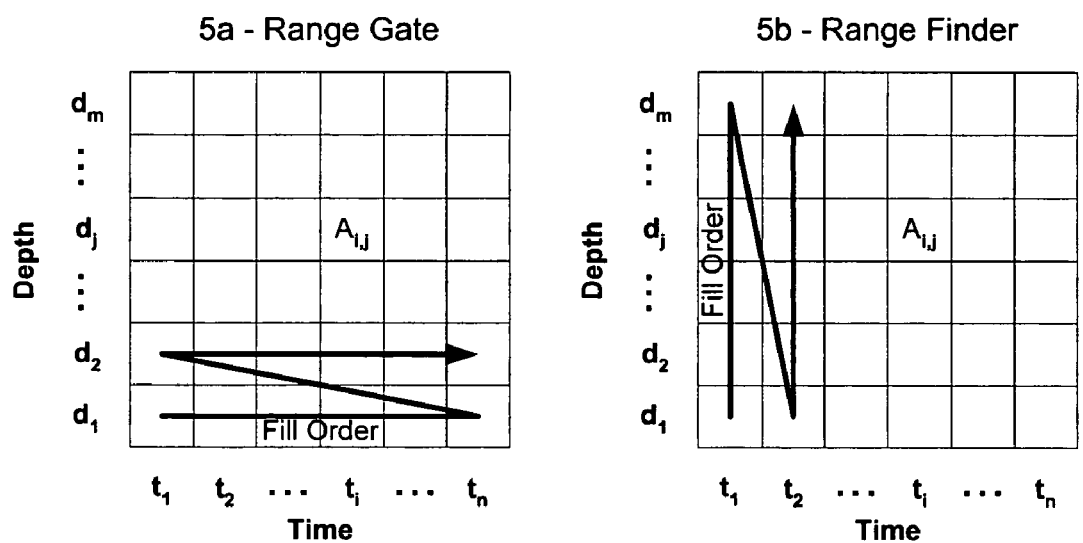
Fig. 5 - Time Domain Reflection Matricies

Frequency Domain Reflection Matrix (72a)

|  | $f_1$ | $f_2$ | ... | $f_i$ | ... | $f_n$ |
|---|---|---|---|---|---|---|
| $d_m$ |  |  |  |  |  |  |
| ⋮ |  |  |  |  |  |  |
| $d_j$ |  |  |  | $C_{i,j}$ |  |  |
| ⋮ |  |  |  |  |  |  |
| $d_2$ |  |  |  |  |  |  |
| $d_1$ |  |  |  |  |  |  |

Depth (vertical axis), Frequency (horizontal axis)

Fig. 7

Max. Amplitude Frequency Coefficient Vector (73a)

| Depth |  |  |
|---|---|---|
| $d_m$ | $f_m(C_m(max))$ | $C_m(max)$ |
| ⋮ | ⋮ | ⋮ |
| $d_j$ | $f_j(C_j(max))$ | $C_j(max)$ |
| ⋮ | ⋮ | ⋮ |
| $d_2$ | $f_2(C_2(max))$ | $C_2(max)$ |
| $d_1$ | $f_1(C_1(max))$ | $C_1(max)$ |

Fig. 8

SYSTEM AND METHOD FOR EXTRACTING PHYSIOLOGICAL DATA USING ULTRA-WIDEBAND RADAR AND IMPROVED SIGNAL PROCESSING TECHNIQUES

FIELD OF THE INVENTION

The field of this invention is medical diagnostic procedures and, in particular, quantitative measurements of physiological functions such as, for example, heart and lung functions. Disclosed is a variant of ultra-wide band (UWB) radar known as micropower impulse radar (MIR) combined with modern signal processing techniques to provide a new type of medical imaging technology.

BRIEF DESCRIPTION OF THE DRAWINGS

FIG. 4 illustrates the general steps of the signal processing used in an embodiment of our invention.

FIGS. 5(a) and 5(b) illustrate two versions of the time domain return signal matrix and their respective fill methods useful in an embodiment of the invention.

FIG. 7 illustrates a frequency domain reflection signal matrix useful in an embodiment of the invention.

FIG. 8 illustrates a Maximum Amplitude Frequency Coefficient Vector.

OVERVIEW

Figure 1:
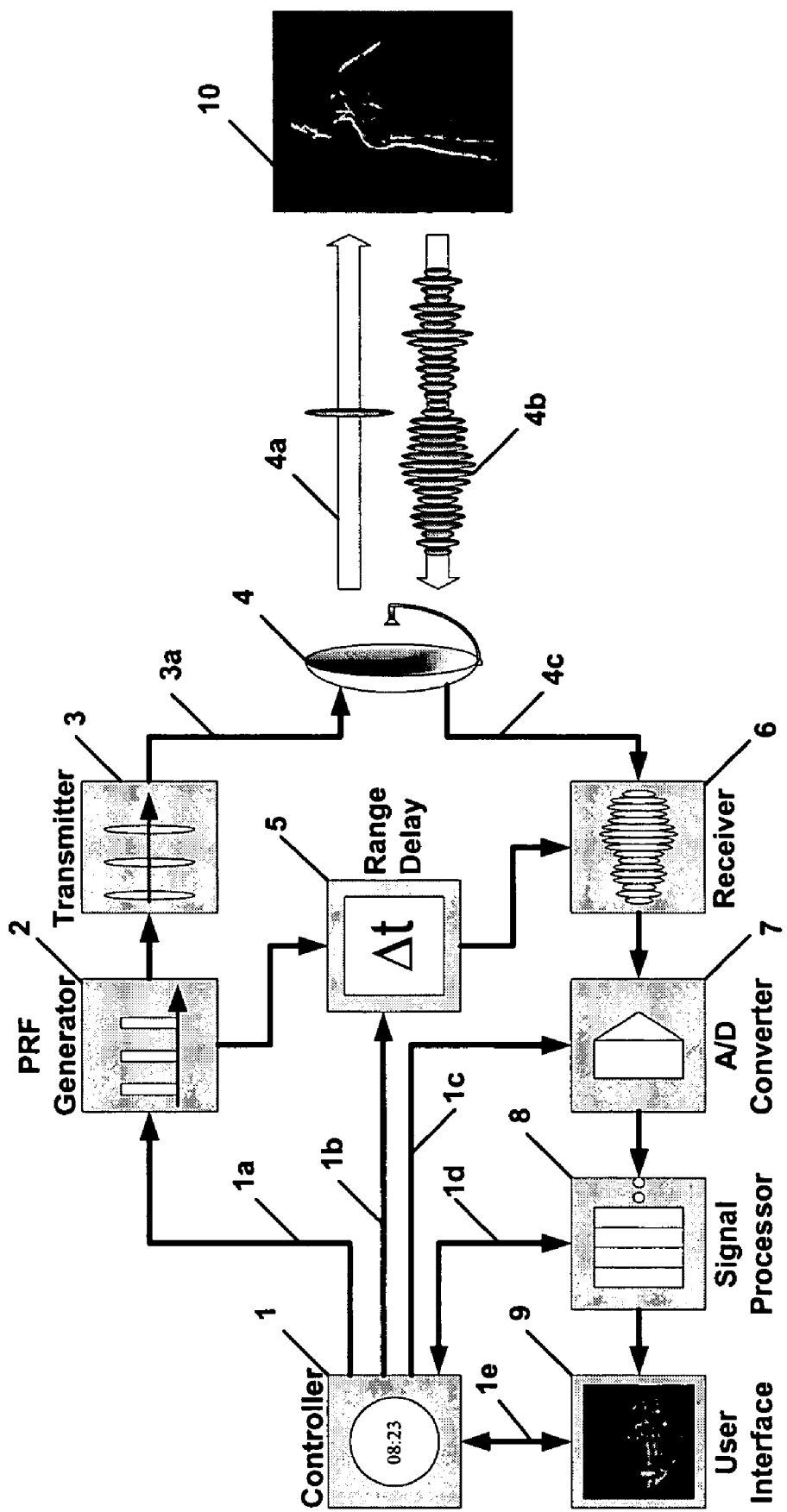
FIG. 1 is a general representation of the overall system architecture useable in an embodiment of the invention.

FIG. 1 shows a system diagram of an embodiment of our invention. In that figure, the controller 1 generates the timing and control signals 1a, 1b, 1c 1d, and 1e to synchronize and manage the rest of the system. It also accepts internal feedback signals from the other subsystems, accepts external control inputs from an operator, and has the capability of providing data outputs to the operator or medical record system. The controller can be realized using an integrated processor and associated circuitry.

Based on timing and control signals 1a from the controller 1, the pulse repetition frequency (PRF) generator 2 creates the baseband pulse train used by the transmitter 3 and, after range delay-$\Delta T$ 5, by the receiver 6. Since the pulse train is common to both the transmitter and receiver subsystems and allows them to operate synchronously, the system is a time-coherent radar system. In practice, a voltage-controlled oscillator (VCO) operating at a nominal but only exemplary output frequency of 2 MHz in or associated with the PRF generator supplies the pulse train. Randomized pulse-to-pulse dither can be added to the output of generator 2 by injecting a noise signal from a noise signal source (not shown) into the VCO control port. The random dither causes spectral spreading to reduce the probability of interfering with other electronic devices as well as provide a unique transmit coding pattern per unit, allowing multiple units to operate in close proximity without substantial concern for mutual interference.

Transmitter 3 generates a series of low-voltage, short-duration pulses 3a (in one embodiment, less than 200 ps) based on the pulse train from the PRF generator 2. In practice, differentiating the edges of a pulse train having extremely fast rising and falling edges creates the sub-nanosecond pulses. Through the combination of the transmitter and the antenna, the short duration pulses are converted into an ultra-wide band spectrum signal centered in the RF/microwave frequency bands in accordance with FCC R&O 02-48.

In this embodiment, the transmitter 3 and receiver 6 share a common antenna though comparable designs could use separate antennas. For the transmitter, the antenna 4 couples the short pulses from the transmitter 3 to the environment, as illustrated at 4a, to patient 5. Subsequently, reflections 4b are received from the environment and fed to the receiver 6. We have tested a variety of antennas ranging from commercially available horns and flat resonators to simple magnetic dipoles. Based on empirical tests, a useful antenna proven to be a magnetic dipole or "loop" antenna with a diameter selected to optimize the transmission and reception of UWB signals. This topology provides adequate gain, broad beam width, and small physical size. For example, a loop antenna with a diameter of 4 cm fabricated from 24-gauge solid copper wire was used in conjunction with a UWB system operating with a 10 dB bandwidth of 1.5 Ghz to 3.4 Ghz.

Based on timing and control signals 1b from the controller 1 and the pulses originating from the PRF generator 2, the range delay-$\Delta T$ 5 generates a delayed version of the PRF timing signal. The output of the range delay triggers a sample-and-hold circuit, described subsequently, in the receiver 6 where the delay value is chosen to compensate for fixed electrical delays within the system and focus data collection to those reflections originating from a specific depth within the body. The range delay is extremely flexible and, in conjunction with the controller, can generate a large range of delay profiles to accommodate a variety of signal processing requirements.

Figure 2:
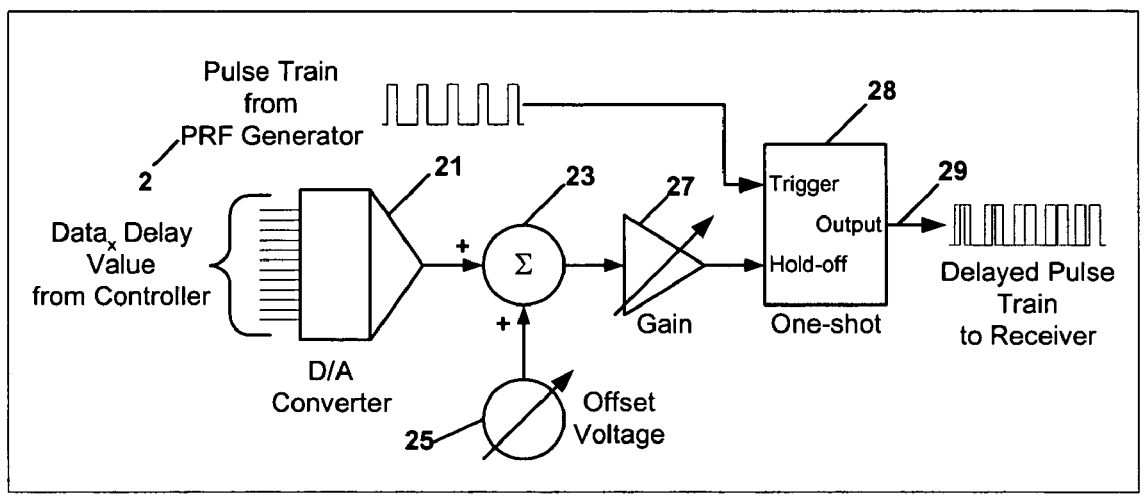
FIG. 2 is a block diagram of a range delay circuit useable in an embodiment of the invention.

There are two delay modes used to collect medical data—range gate mode and range finder mode. In range gate mode, the depth within the body that corresponds to the area for which physiological data is to be extracted is fixed and a large number of samples are collected at that depth over a period of multiple seconds in one example, providing information on relative changes within the body. The depth can then be changed and the process repeated. In contrast, when operating in range finder mode, the depth is swept repeatedly over a finite range of interest, with samples collected at each depth. Range gate mode provides detailed information at the depth of interest while range finder mode is used to quickly collect data over a range of depths. The range delay circuit of FIG. 2 supports both range gate and range finder modes. In practice, the range delay circuit can be realized using a 12-bit digital-to-analog converter (DAC) 21, an operational amplifier, used to realize functions 23, 25, and 27, and a one-shot multivibrator 28. The one-shot multivibrator (an LMC555 can be used, as one example) generates a delayed version of the transmitted pulse train in response to signals received on its two control inputs—trigger and hold-off. The pulse train from the PRF generator 2 of FIG. 1 is the trigger signal and causes the one-shot multivibrator to initiate a single pulse cycle for each pulse in the pulse train. The hold-off voltage determines the period of the pulse. By varying the hold-off voltage, different pulse periods, and thus different delay values, can be generated. The amount of delay is set by both analog and digital controls. The analog controls set the minimum delay value and the allowable range of control while the digital controls are used to dynamically adjust the actual delay value, delay sweep rate, and resolution of delay control.

In practice, a 12-bit data value—Data$_x$, corresponding to the desired delay is sent from the controller 1 to the DAC 21. The DAC produces a voltage V$_x$ where:

$$V_x = 4.096 \text{ Volts} \times (\text{Data}_x/4096)$$

The DAC output voltage 21 and a DC voltage 25 are added together in a summing junction 23 and the sum is amplified and fed to the hold-off control input of the one shot 28. The DC voltage level, in conjunction with the amplifier gain, set the minimum delay value and the allowable range of control. Both the DC voltage level and gain settings are controlled by manual adjustment of potentiometers. A delay range of 5 ns has been proven to yield good quantitative data in cardiopulmonary applications and corresponds to a depth range of approximately 12 cm into the body. Other delay range values of up to 10 ns have also shown to produce usable data sets.

The receiver 6 processes the raw reflections received from the antenna 4 over line 4c in the analog domain to optimize the signals of interest. For cardiopulmonary data, this includes suppressing the high-strength static return signals and amplifying the motion artifacts. Receiver 6 is illustrated in detail in FIG. 3 and can be based on a dual-channel balanced receiver architecture where the transmitter pulses are capacitively coupled from the output of the transmitter 3 into both receive channels 30a and 30b via RF Splitter 30 and the antenna 4 is connected or otherwise coupled to one channel 30a. The balanced receiver architecture provides a high degree of common mode rejection as well as differential gain. The common mode rejection provides a significant amount of attenuation to signals common to both channels thus minimizing interference from the transmit signal with the desired receive signal. The differential gain inherent in this architecture amplifies signals unique to either channel thus the received signal, being unique to channel 30a, is amplified.

Both channels 30a, 30b can use an ultra-fast sample-and-hold (S/H) circuit 32a and 32b each triggered by the delayed impulse train created by the pulse generator 31 using the delayed pulse train over line 29 from the range delay circuit-ΔT 5 of FIG. 1. The active sampling window is set at approximately 320 ps in one example and can be easily modified by selectively changing the value of a single passive component. The outputs of the two S/H circuits are integrated over multiple samples in integrator elements 33a and 33b to improve the signal-to-noise ratio. The integrated samples feed the inverting and non-inverting inputs of an instrumentation amplifier 35, attenuating the transmitted signal and amplifying the received signal.

Figure 3:
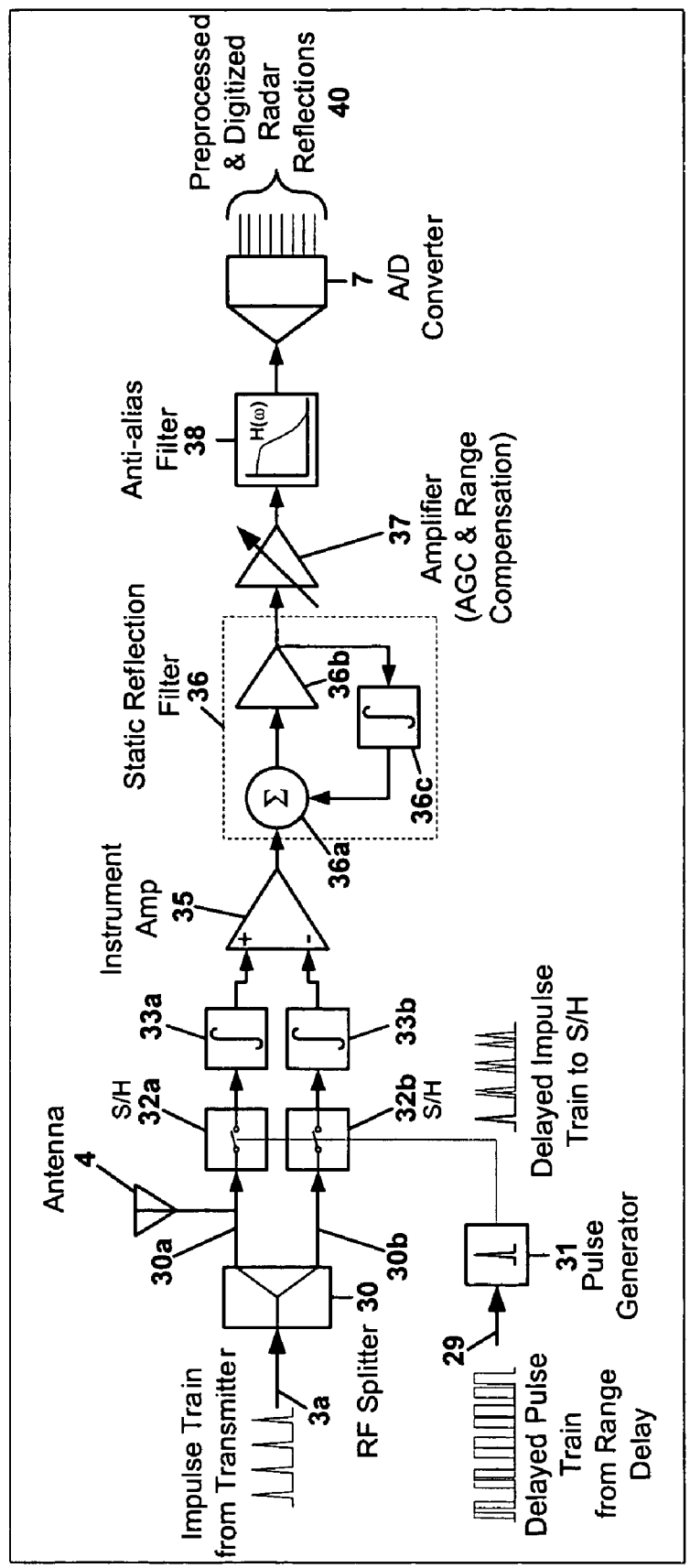
FIG. 3 is a block diagram of a balanced receiver useable in an embodiment of our invention.

Additional circuitry in the receiver incorporates several key pre-processing functions including static reflection suppression in filter 36, amplification in amplifier 37, and anti-alias filtering in filter 38. We have tested two basic techniques for suppression of static reflections: feed-forward and feed-back circuitry. In the feed-forward case, the output of the instrumentation amplifier 35 is applied to the input of a low-pass filter (F$_{cutoff}$≦0.2 Hz) to attenuate frequency components related to organ movement in the patient. The filtered signal is subtracted from the original output yielding a difference signal with reduced static reflection components. The difference signal is amplified to further enhance the desired signals with respect to the static reflections. A diagram of the receiver with the lowpass feedback static reflection filter 36 is shown in FIG. 3. In the feedback case, a low-pass filter 36c is used as the feedback element. Again, the corner frequency of the filter is chosen to attenuate the motion artifacts. The resulting signal out of the low pass filter primarily contains the static reflections, which are subtracted from the incoming signal. This circuit significantly increases the signal-to-noise ratio for motion artifacts by attenuating the unwanted static return signals that would otherwise swamp out the motion components.

The amplification stage 37 is composed of two parts in our example,—range compensation and automatic gain control (AGC). The range compensated gain circuit compensates for received energy loss as the distance from the antenna to the depth of interest increases by increasing the gain over the delay sweep time. This block also includes selective blanking (38 dB of attenuation) capability to eliminate undesired reflections. It can be used, for example, to mask antenna reflections due to impedance mismatch by attenuating all received signals over a specific range. Range compensated gain can also be disabled in favor of fixed gain. The AGC amplifies the small-signal radar return signals to achieve maximum dynamic range prior to the digitization process, explained subsequently. The gain of the amplification stage has an adjustment range of −38 dB to +38 dB.

The final preprocessing stage includes the anti-aliasing circuitry 38. The preprocessor low-pass filters the optimized data to minimize the potential of aliasing at the digitization stage. As indicated by accepted signal processing techniques, the pass-band characteristics, bandwidth, and order of the low-pass filter are selected to attenuate those frequency components at or above half the sample frequency (i.e., Nyquist frequency) to below the resolution of the analog-to-digital converter while minimizing distortion of the desired frequency components, as is well known in the art. For example, the variables in the anti-alias filter design problem are the 3 dB cut-off frequency of the filter ($f_{LPF}$), the order of the filter (n), and the sample frequency ($f_S$). Usually the 3 dB cut-off frequency of the filter is selected to provide minimal attenuation of the desired frequency components related to the physiological event. It may also be set as low as possible or appropriate to reduce the corresponding sample rates in the digitization process thereby avoiding large amounts of redundant data. With the 3 dB cut-off frequency of the filter determined, it is up to the designer to evaluate the interdependence between the filter order and sample frequency and arrive at acceptable values for each.

As an illustrative example of the anti-alias filter design process, the human cardiopulmonary frequency spectrum is band-limited to less than 5 Hz, corresponding to a maximum cardiac rate of 300 beats per minute. Basing the design around a 16 bit analog-to-digital converter having 65,536, that is, ($2^{16}$), possible output states, the attenuation at the Nyquist frequency is calculated by:

$$\text{Attenuation at } f_{Nyquist} \leq 20 \log_{10}(65{,}536) = 96.33 \text{ dB};$$
$$\text{where: } f_{Nyquist} \leq f_{sample}/2$$

Settling the 3 dB cut-off frequency of the filter at twice the highest frequency component in the signal of interest to minimize distortion and based on the approximation of 6 dB of attenuation per filter pole yields the following table:

TABLE 1

Attenuation versus Number of Filter Poles

| Number of Poles | Attenuation at 9600 Hz (4 octaves above 600 Hz @ 24 dB/pole) |
|---|---|
| 2 | 48 dB |
| 3 | 72 dB |
| 4 | 96 dB |
| 5 | 120 dB |

In this case, a fourth-order low-pass filter with a 3 dB cut-off frequency of 600 Hz will provide approximately 96 dB of attenuation for frequencies above 9600 Hz. The corresponding sample rate can be set to any convenient value greater than 19200 Hz (2×9600 Hz). Other filters can be employed to support a variety of sampling schemes.

As illustrated in FIG. 1, the ND converter 7 (ADC) is controlled by Controller 1 through control lines 1c. The controller sets the sample rate, sample resolution, and start/stop timing for the sampling process based on the mode of operation. The ADC digitizes the enhanced analog motion reflections from the receiver 6, as described with respect to FIG. 3, translating the enhanced reflected energy into a series of discrete digital values. As one example in range gate mode, we have used 16,000 samples per second at 16-bits per sample.

The digitized signal from the A/D converter 7 is then processed to extract pertinent physiological information in signal processor 8 per FIG. 1. The signal processing block is extremely flexible and, as mentioned previously, can accommodate a wide variety of algorithms in support of different medical applications. In addition the algorithm can be implemented using parallel, serial, or hybrid parallel/serial architecture. The choice of a specific architecture is left to those skilled in the art and will depend on the application and other system constraints. The controller manages the signal processing operations through control path 1d.

The resultant physiological data is displayed on the User Interface 9 (UI) of FIG. 1. This can include tracings of amplitude versus time for one or more depths of interest, power spectral density for one or more depths of interest, time domain and frequency domain histograms for a range of depths, numerical values for heart and/or lung rates, as well as the associated confidence factors for the displayed data, as described subsequently. The Controller 1 of FIG. 1 converts the data from the signal processor to an operator-friendly format through control path 1e for display on the UI.

Signal Processing

The signal processing block 8 of FIG. 1 can comprise the three blocks shown in FIG. 4. The three blocks of FIG. 4 can be implemented entirely in software on the Signal Processing block 8 of FIG. 1 in our embodiment. Other implementations of these signal processing techniques and their location within the system can be made without departing from the spirit or scope of the invention. The Extractor block converts the digitized MIR reflections into a variety of useful physiological data including cardiopulmonary data such as cardiac and pulmonary rate and rhythm (i.e., trending). The Analyzer block processes the time-ordered sequence of values and confidences measures from the Extractor and searches for problematic trends in the values. The Focuser block is a control process that uses the results from one or more of the device's stages to modify the amount and types of processing performed on each pass through the system.

The input to the signal processing stage is the preprocessed and digitized reflections produced by the ADC. The signal processor stores the ADC output in a two-dimensional matrix of time-sampled reflection values to support subsequent operations. In both FIGS. 5a and 5b, the time domain reflection matrix is organized with the columns contain data collected at a specific sample interval with respect to the synchronization signal and the rows contain data collected at a fixed depth. The order of the digitized values depends on the mode of operation—i.e. range gate or range finder. For range gate mode as illustrated in FIG. 5a, the digitized values are organized as a series of contiguous values obtained at a fixed depth, providing information on relative changes within the body for a specific depth. When the depth or range gate setting is changed, a new series of contiguous values is produced. For range finder mode as illustrated in FIG. 5b, the digitized values are organized as a series of values obtained for a monotonically increasing depth or range. A new series is generated for each sweep through the depth or range of interest. The matrix could be three-dimensional if more than one MIR device is used simultaneously. For example, two synchronized MIR devices positioned at two different points on a patient's chest.

Extractor

The Extractor 44 of FIG. 4 operates on the time domain reflection matrix to extract a variety of useful physiological data including cardiopulmonary data such as cardiac and pulmonary rate and rhythm (i.e., trending). It is also extensible to measurements of many other physiological data collection applications including measurement of parameters associated with cardiac chamber volume—e.g. stroke volume, ejection fraction, cardiac output, and the like. The Extractor 44 can operate on either data files collected at an earlier time or continuous data captured in real-time. It utilizes one or more control loops that can restrict the incoming data to a particular area for improved computing efficiency or enhanced detail extraction. In one embodiment, the Extractor 44 is implemented entirely in software that runs on the Signal Processor block 8 of FIG. 1.

Figure 6:
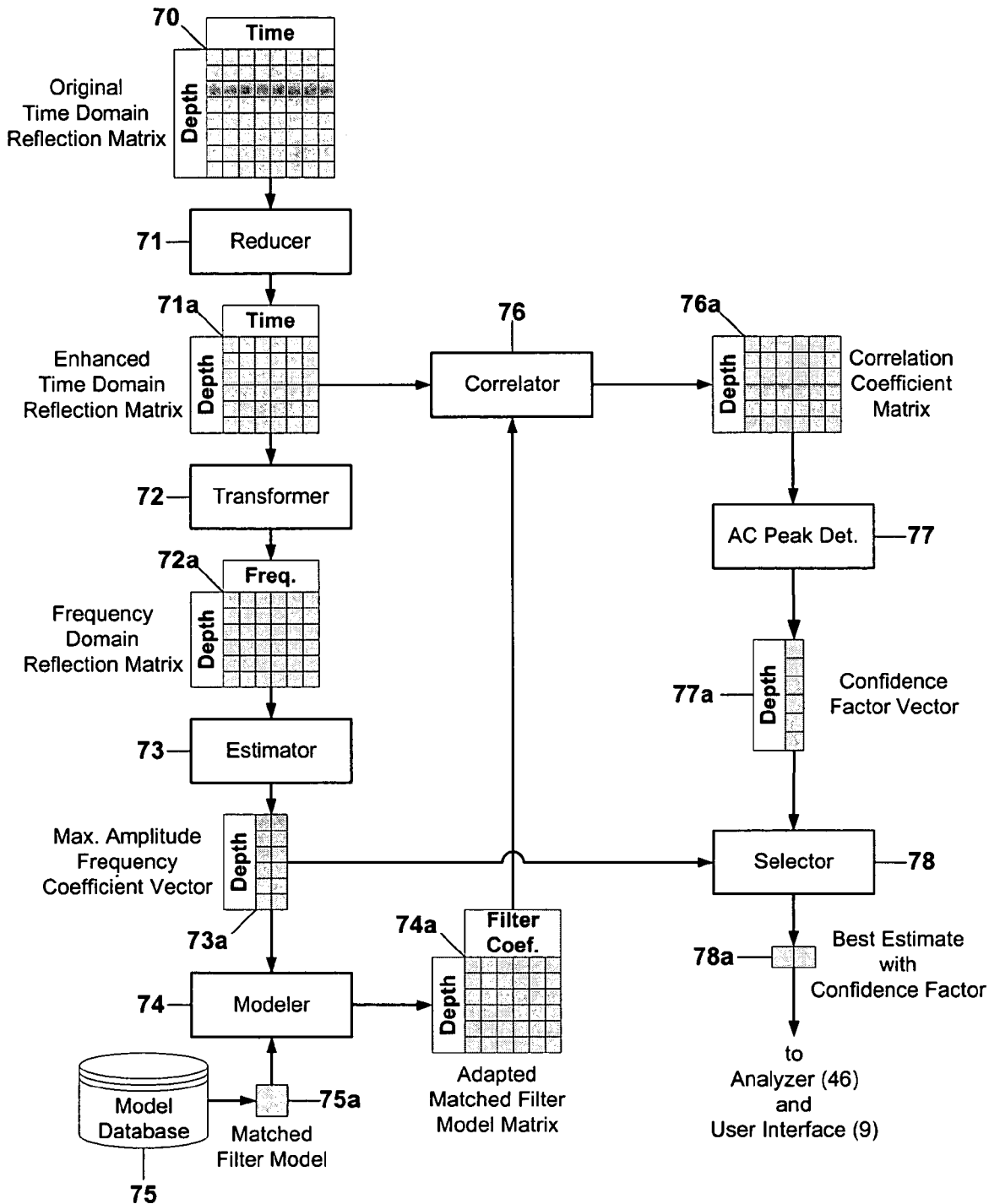
FIG. 6 illustrates general signal processing steps used in an embodiment of our invention.

FIG. 6 shows the processing steps of the extractor and the data structures produced by each step. In the preferred embodiment, we elected to implement a serial architecture because we were interested in collection of a single type of physiological data. The extractor could have been realized by a parallel design. A parallel design might be appropriate for those applications using multiple MIR devices, collecting a variety of data types, or requiring a variety of filter models. The following subsections describe the purpose of each processing step in the extractor.

Reducer

The Reducer 71 of FIG. 6 is the first stage in the Extractor. It receives the preprocessed and digitized reflections produced by the ADC stored in the time domain reflection matrix 70. The operations (either one-dimensional or two-dimensional) performed in this stage further refine the data to optimize specific parameters. For example, in those applications where detection of movement is desired such as cardiac rate, a helpful operation involves reducing the contribution of static reflections. The static reflections are attenuated by subtracting the time domain date from an average. The average used for the differencing can be as simple as the first stored row in the time domain reflection matrix to an actual average calculated from multiple rows in the matrix. In practice, we have found that an average calculated from 8 rows provides sufficient attenuation of the static reflections to enable accurate detection of cardiac movement.

Other operations can include sub-sampling (with or without interpolation) to reduce the volume of time-sampled data, coarser quantization to increase contrast and reduce computational complexity, and normalization to maximize dynamic range. In addition, some of the data rows in the time domain reflection matrix may be deleted if the Focuser feedback mechanism 48 of FIG. 4 determines that reflections from those depths do not contain useful data or improve the quality of the measurements. The Focuser is described subsequently. The output of the reducer stage is a second two-dimensional matrix containing enhanced time-sampled reflection data 71*a* shown in FIG. 6.

Transformer

The transformer step 72 of FIG. 6 converts the enhanced time-sampled reflection data produced by the reducer to the frequency domain for spectral processing. The following table lists several common techniques typically used to implement the transform.

Discrete Fourier Transform (DFT)—a complex time-to-frequency domain transformation most commonly implemented using a Fast Fourier Transformation algorithm.

Discrete Cosine Transform (DCT)—similar to the DFT, the DCT is a real time-to-frequency domain transformation used extensively image and video compression.

Discrete Filter Bank (DFB)—a set of bandpass filters where the individual pass bands are selected to separate the signal into specific frequency ranges of interest.

The actual transform used will depend on the application and system processing capabilities. For example, an inexpensive device used to collect basic cardiac rate and rhythm data for physical conditioning might employ the DCT while a more life-critical device for monitoring the condition of individuals suffering from coronary heart disease might require the added precision of the FFT. A system using the DFB would provide a method for determining when a specific physiological parameter deviates from an acceptable range.

The transformed reflections are still in a 2-dimensional matrix 72*a*, but the time dimension has been translated into frequency and the value in each cell corresponds to the transform coefficient at a given depth. In the case of a real transform—e.g. the DCT or DFB, each cell will contain a single coefficient that corresponds to the amplitude of the energy contained in the original time domain signal for the given frequency. If a complex transform—i.e. an FFT, is employed, the value in each cell will be complex coefficient, having a real and imaginary component that may be converted to magnitude and phase through standard trigonometric identities. FIG. 7 shows the frequency domain reflection matrix format where one axis corresponds to the depth of the sample while the other axis corresponds to the frequency. The frequency domain reflection matrix is used in subsequent phases of the Extractor.

Estimator

Figure 9:
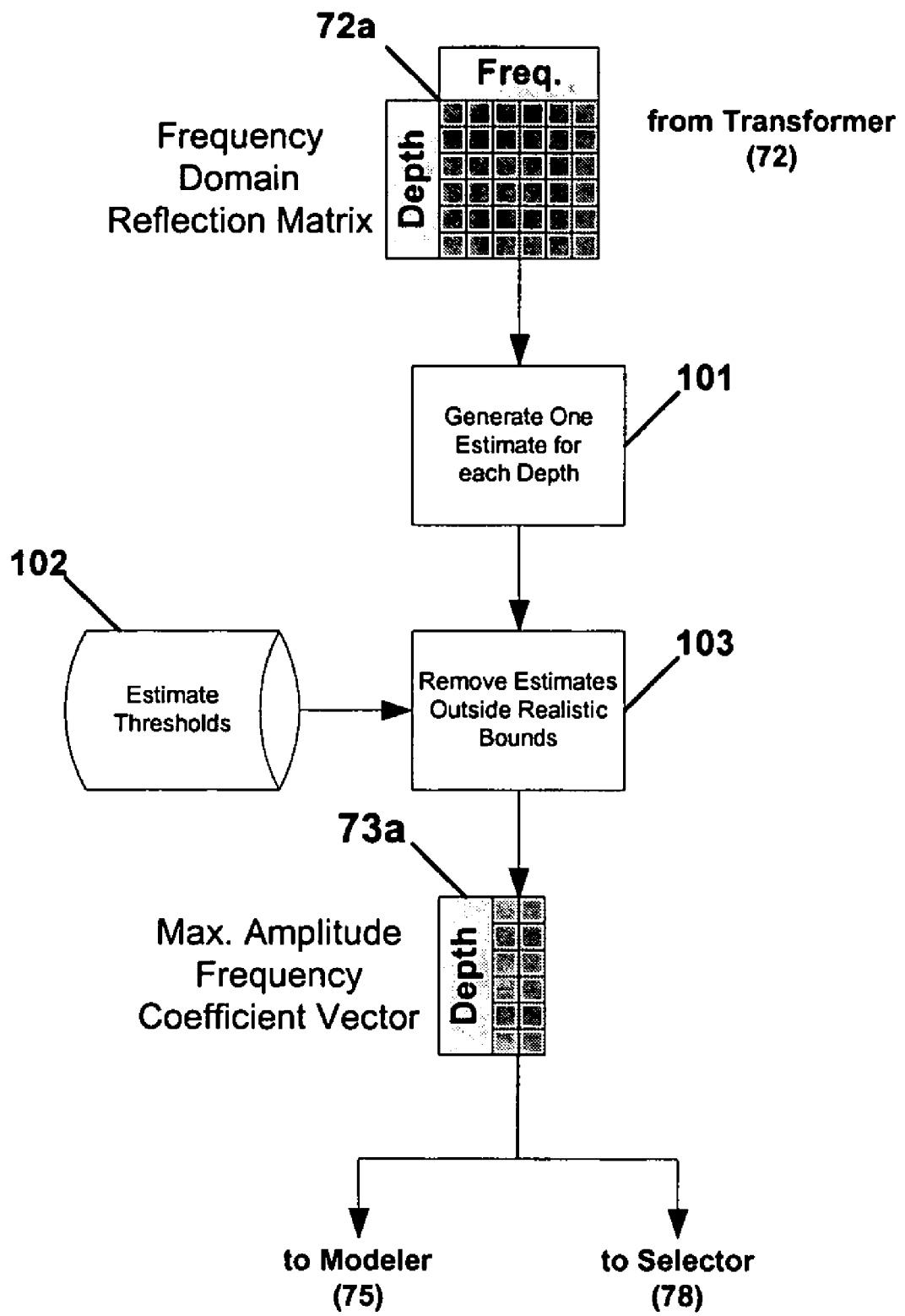
FIG. 9 illustrates a block diagram of the Estimator of one embodiment of our invention.
Figure 10:
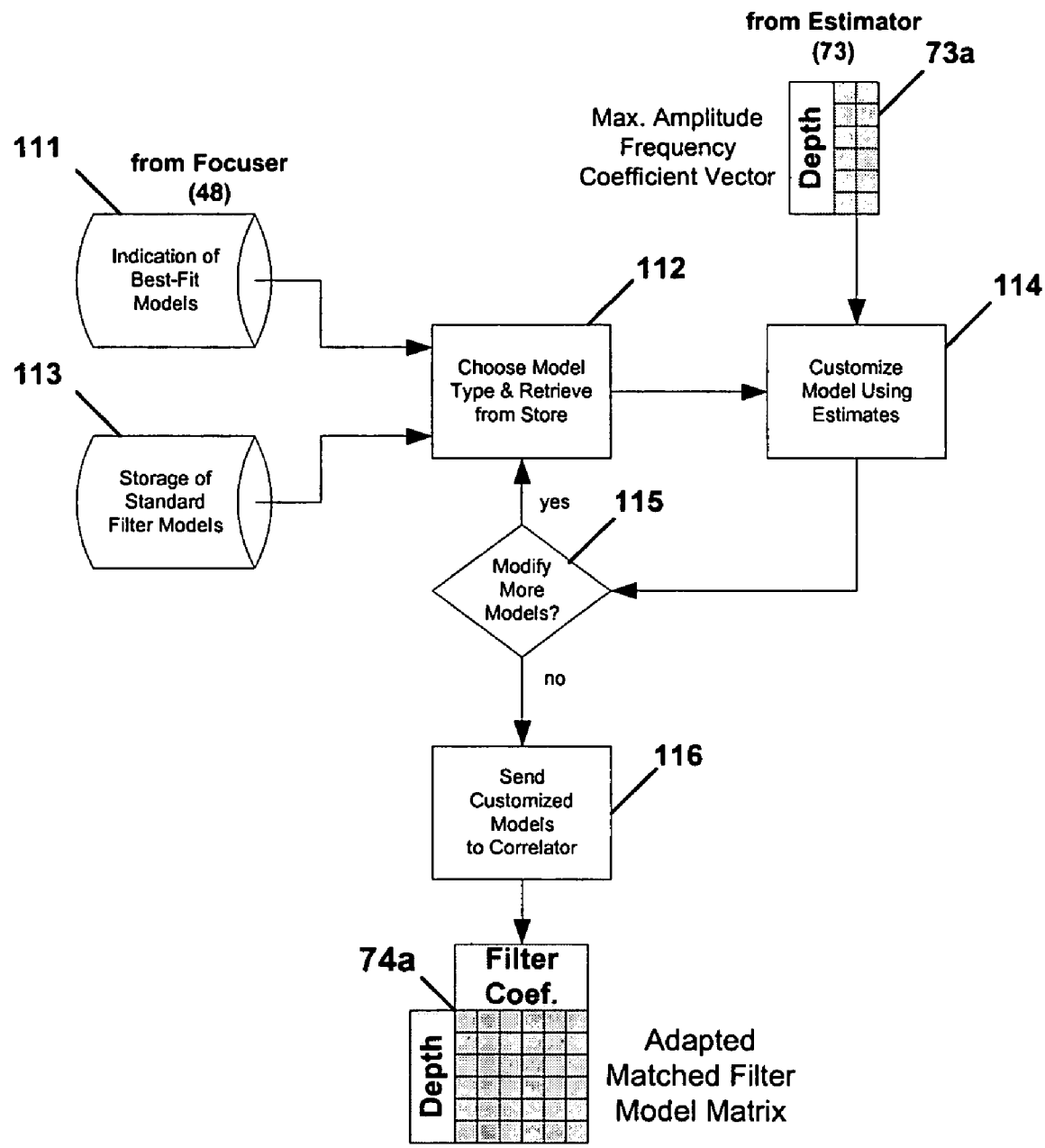
FIG. 10 illustrates a flow chart showing the modeler and the operation of modeler signal processing useful in an embodiment of our invention.

As detailed in FIG. 9, the Estimator 73 of FIG. 6 operates on the frequency domain reflection matrix 72*a* of FIG. 6 to derive an approximate value for the physiological process under investigation for each depth of study so that suitable models can be selected and optimized in the next step (the Modeler 74 of FIG. 6). In addition, the approximate values are forwarded to the "Selector" step 78, which will ultimately determine the optimal measurement. The Estimator, Modeler and Selector can be implemented entirely in software running on the Signal Processor 8 of FIG. 1.

To derive the above approximate values, the estimator creates a two-dimensional vector 73*a* of FIG. 6, as shown in detail in FIG. 8 of length equal to the number of depths under investigation. The values stored in the vector for each depth is equal to the frequency having the highest amplitude coefficient at that depth and the amplitude of the coefficient. The pseudo-code below illustrates a sample "maximum value" search algorithm used to find the maximum amplitude coefficient and its corresponding frequency for each depth under investigation. Last, this vector may be filtered to remove those frequency values that are outside the range of nominal or expected values for each process under investigation. For example, in the investigation of cardiac rate, only those frequency values between 0.5 Hz and 5 Hz are of interest (corresponding to 30 beats per minute to 300 beats per minute). All values outside this range can be eliminated. The use of a post-estimator filtering step operates only on the estimation vector and preserves the original frequency domain reflection matrix so that multiple physiological processes can be investigated simultaneously on the same data set. The filtered vector from the estimator is available for subsequent operations.

Sample Pseudo-Code for Identifying Maximum Amplitude Frequency Coefficient

| | |
|---|---|
| For j = 1 to M | ;Loop over all depths |
|   Let Max(j) = C(1,j) | ;For depth "j", initialize max amplitude to first amplitude |
|   Let Freq(j) = 1 | ;For depth "j", initialize frequency of max amplitude to 1st freq. |
|   For I = 2 to N | ;Loop over all frequencies at depth "j" |
|     If C(i,j) > Max(j) | ;Search for and store max amplitude and corresponding freq. |
|     Then { Set Max(j) = C(i,j) And Set Freq(j) = I } | |
|     Else | |
|   Next i | ;Repeat across all frequencies |
| Next j | ;Repeat across all depths |

This process is extensible to generating frequency signatures through more sophisticated sorting of the frequency data and calculating statistics on the distribution of the coefficients. For example, once the maximum frequency coefficient is known, one could gain further information about the process under investigation through calculation of the standard deviation of the variation in amplitudes of the other frequency coefficient from the maximum. In addition, more than one physiological process can be estimated on each pass. In that instance, multiple filtered vectors would be produced, one for each physiological process. For example, estimates for cardiac and pulmonary rates could be generated from the same underlying frequency data.

Modeler

For each estimate vector produced by the Estimator 73 of FIG. 6, the Modeler 74 adapts one or more matched filters from its Filter Model database 75 into one or more vectors of matched filters 74*a* for subsequent cross-correlation with the original time-based reflection data. The database contains one or more matched filters that were developed from a single cycle of the physiological process under investigation. An individual matched filter 75*a* is developed by self-convolving a single cycle pattern to produce a matched filter for that pattern. The formula used to create a matched filter—designated by MF(n), from a discrete pattern of length N—designated by P(n), using the discrete form of convolution is:

$$MF(n) = \sum_{m=0}^{m=N} P(m)P(n-m)$$

The single cycle patterns used to generate the matched filters can be based on simple periodic waveforms (e.g., a half-cycle sinusoid), more complex patterns developed through theoretical studies of expected reflections, or actual captured patterns from individual patients. The database can include filters representing normal cycles as well as abnormal cycles resulting from a variety of ailments. The input patterns could be captured as part of a fitting or calibration process. The actual selection of filters used to populate the database is expected to be application dependent.

As an example, for a system that measures cardiac rate and rhythm, the database would contain filters based on various single cardiac cycles. The filters in the database may include entries based on a half-cycle sinusoid, ideal normal patterns, patterns captured from a patient, and abnormal patterns corresponding to bradycardia, tachycardia, and fibrillation. The application of multiple filters allows the system to select the filter that better "matches" the incoming reflections, improving tracking of the process under observation and supporting identification of normal and abnormal patterns. The process of evaluating the degree of "match" and filter selection is handled by subsequent operations.

With a database containing one or more matched filters, the Modeler 74 uses the frequency coefficient vector from the Estimator 73 to generate a first-order estimate of the cardiac rate for each depth in the vector and adapts the filters in its database to the estimated rate through expansion or contraction of the period of the single cycle models. This can be looked upon as customization. For example, suppose the matched filter is based on a half cycle sinusoid with a nominal period of 1 second (equivalent to 60 beats per minute) and the estimate for depth N is 0.75 seconds (equivalent to 80 beats per minute). The original matched filter stored in the database would have a period of 2 seconds since it is twice the length of the pattern used in the self convolution and the adapted filter would have a period of 1.5 seconds. As the Estimator is enhanced to produce more sophisticated estimates, the Modeler can be modified to support adjustment of additional matched filter parameters. For example, as the resolution of the underlying system is increased, it may be possible to differentiate between atrial and ventricular activity. The timing between these two types of events may prove to vary for different individuals or medical conditions. Adaptation of the matched filter to account for variations in both overall period as well as atrial/ventricular spacing may provide more accurate or medically significant data.

Feedback from subsequent steps in the overall algorithm may eliminate some matched filters from consideration because the measurements derived from them are of consistently poor quality compared to other models. For example, if the modeler is using a sinusoid and a square wave as the basis for its two matched filters and it is determined that the filter derived from the square wave consistently gives poor results (i.e., unrealistic measurements) compared to the sinusoid, the square wave model will be dropped from consideration. Conversely if the system had previously reduced the number of filter types to a single model and the quality of the data began to degrade, the system may decide to apply multiple models in an attempt to find a better match. This feedback mechanism is handled by the Focuser 48 of FIG. 4.

In the implementation shown in FIG. 9, the modeler is realized using a serial architecture requiring multiple passes to complete all calculations. It may model more than one physiological process per invocation. In block 114, the estimates for the i-th physiological process being measured are received from the Estimator 73. In block 112, matched filter(s) are selected from the database of filters 113. Feedback from the Focuser 48 on which filters have been providing the best results is provided through block 111. Block 112 may use this feedback to eliminate one or more filters from consideration. Once the set of filters (one or more) have been chosen, they are each customized in block 114 based on the estimates received from the Estimator. Customization is discussed more fully two paragraphs above. Decision block 115 causes each filter to be customized in turn until they are all done. At that point, the customized filters are forwarded to the Correlator 77 in block 116. These steps are run for each physiological process being measured. For example, given estimate vectors for cardiac and pulmonary rates, it would produce a set of matched filters for both processes where each filter set may contain one or more filter types with each type adapted for every depth represented in the estimate vector.

Correlator

The Correlator 76 of FIG. 6 utilizes the concept of matched filters and correlation to calculate a matrix of correlation coefficients for the measurements of the physiological process under investigation. The Correlator can be implemented entirely in software running on the Signal Processor 8, if desired. The vector, or set, of adapted filter models 74a from the Modeler 74 is cross-correlated with the enhanced time-based reflection matrix 71a from the Reducer 71 to produce a series of correlation coefficient matrices with one matrix per matched filter model vector. The cross-correlation of a single matched filter MF(n) of length N and the data from depth $D_i$ of length M is given by the following formula:

$$R_{MF,D_i}(p) = \sum_{m=0}^{m=M} MF(m)D_i(p+m); \text{ for } p \subset (-N, M)$$

Figure 11:
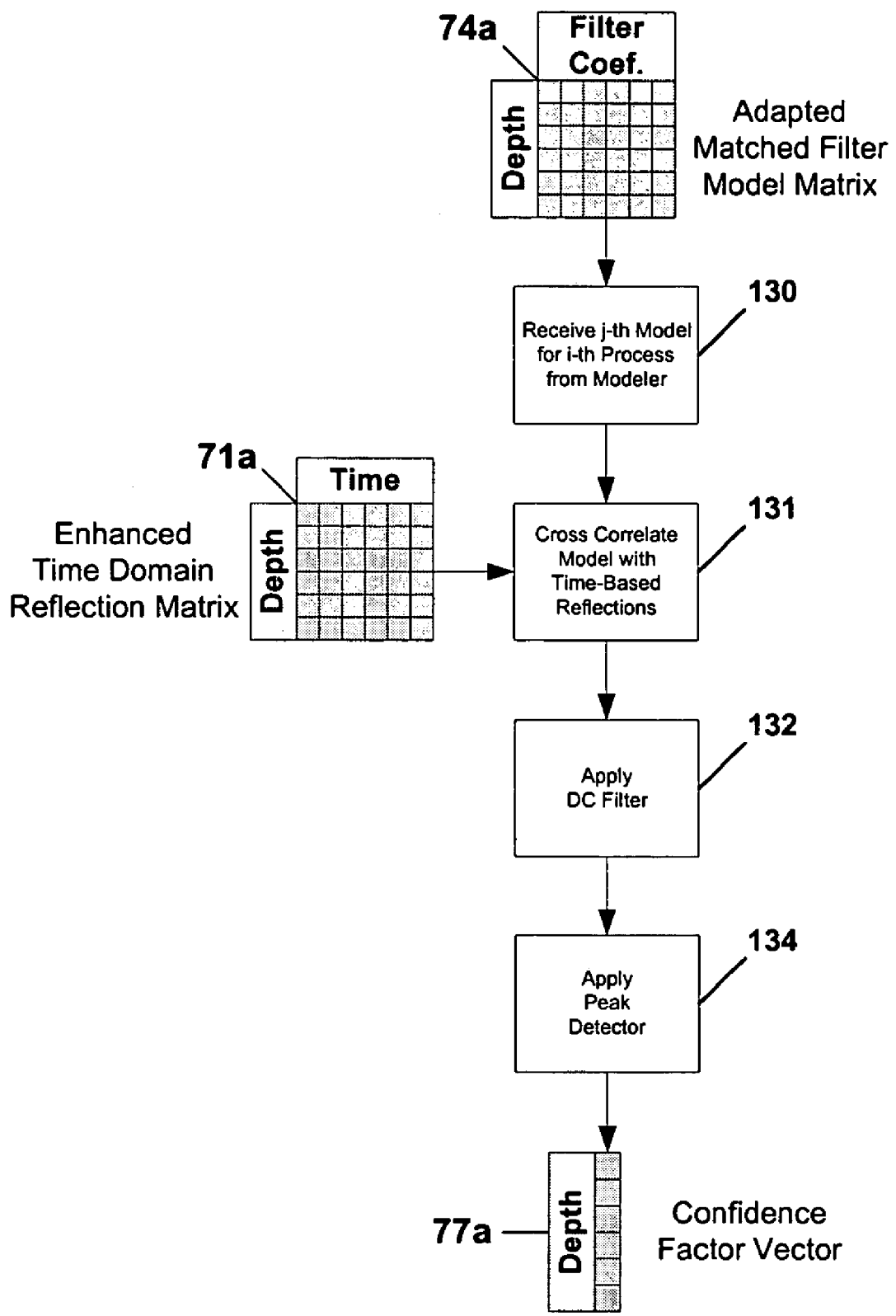
FIG. 11 illustrates a flow chart of the correlator and correlator signal processing useful in an embodiment of our invention.

The Correlator may receive more than one customized model for each physiological process being measured. FIG. 11 illustrates the processing blocks in the Correlator for one filter model applied against one physiological process. In block 130, the i-th model for the j-th physiological process is received from the Modeler 75. That model is cross-correlated in block 131 with the enhanced time-based signals. That is, the i-th model for the j-th physiological process at the k-th depth is cross-correlated with the enhanced time-domain data for depth k.

AC Peak Detector

The AC peak detector 77 shown in FIG. 6 operates on each row of the correlation coefficient matrix 76a from the Correlator 76. Each row in the correlation matrix is DC-filtered to remove any common bias. The resultant filtered rows are run through a peak detector, where the peak value for that row represents the confidence or "degree of fit" of the matched filter to the reflection data. The larger the magnitude of the peak value the better the match and the more confidence that the filter model and adaptation accurately characterize the reflection data. The computed output of the Correlator is a vector of confidence factors 77a, where the vector contains one confidence factor for each depth in the enhanced time-domain reflection matrix.

After cross-correlation, the DC Filter is applied in block 132 and the Peak Detector is applied in block 134 of FIG. 11. The peak value determined becomes the confidence metric for the estimate (as found by the Estimator). The peak values, one at each depth for each physiological process, are sent to the Selector 78.

The Correlator may perform more than one correlation per invocation. For example, it may correlate a model for cardiac rate and one for pulmonary rate, producing a unique confidence metric for each process at each depth.

Selector

The last stage in the Extractor 44 of FIG. 4 is the Selector 78 of FIG. 6. For each physiological process under investigation, the selector takes the estimates from the Estimator 73 and the set of confidence measures 77a from the AC Peak Detector 77, seen in FIG. 6, as input and produces a single "best fit" measure with a corresponding confidence metric. A best fit measure and confidence metric pair are the output for each invocation of the above Selector algorithm operating on a single time-domain reflection matrix. This generates a pair of time ordered sequences as illustrated in the example below. The M's in the measurement sequence represent the time-ordered measurements of the physiological process being measured. The Q's represent the corresponding confidence of each measurement.

If more than one physiological process is under investigation, the Selector may choose more than one value per invocation; depending on how many value-confidence matrices it is given from the Correlator step. For example, it may select a value for cardiac rate and one for pulmonary rate.

Selector Output for Process M:

Analyzer

The Analyzer 46 of FIG. 4 processes the time-ordered sequence of values and confidence measures from Selector 78 of FIG. 6 and seeks for problematic trends in the values. It can detect trends because, under normal circumstances, a time-ordered sequence of measurements of a physiological process should remain within a specific range and any variations should correspond to one of many well-known patterns. Excursions beyond appropriate ranges or deviations from expected patterns may signal a problematic trend. For example, while resting, a person's cardiac rate should be low and exhibit little variation. As the level of activity increases, their cardiac rate will increase gradually. On the other hand, an exceedingly high heart rate or a rapid increase in heart rate may indicate that the person being monitored is experiencing a cardiac event.

A second technique is based on time series analysis where the next incremental value in the series is predicted from one or more past values and then, when the actual value arrives from the Selector, the difference between it and the prediction is calculated. This difference is the first order prediction error and suitable error thresholds can be applied to the error terms. There are many techniques used in practice to calculate the prediction term with one of the most common based on the application of a "moving average filter of degree N" where the N most recent measurements are averaged and this average becomes the prediction of the next measurement. This process is illustrated below.

Original Measurement Sequence to time (n): $M_{-3}, M_{-2}, M_{-1}, M_0, M_1, M_2, M_3, M_4, \ldots, M_n$, Corresponding minimum and maximum thresholds on Measurement M: $(M_L, M_H)$ Generation of (n+1) prediction: $M^*_{n+1}=f(M)$; where f is a function operating on one or more past values of M Calculation of (n+1) error term: $E_{n+1}=M_{n+1}-M^*_{n+1}$

| Measurement Sequence: | $M_{-3}$ | $M_{-2}$ | $M_{-1}$ | $M_0$ | $M_1$ | $M_2$ | $M_3$ | $M_4$ | ... | $M_n$ | $M_{n+1}$ | ... |
|---|---|---|---|---|---|---|---|---|---|---|---|---|
| Confidence Metric Sequence: | $Q_{-3}$ | $Q_{-2}$ | $Q_{-1}$ | $Q_0$ | $Q_1$ | $Q_2$ | $Q_3$ | $Q_4$ | ... | $Q_n$ | $Q_{n+1}$ | ... |

On each invocation of the Selector, the simplest method for selecting the "best fit" measurement is to choose the one with the greatest confidence metric. However, this scheme may be enhanced by considering confidence metrics at the depths adjacent to the depth with the largest confidence magnitude. Depths with high confidence metrics but low adjacent confidence metrics may be discarded in favor of a depth centered in an area with generally-high confidence metrics.

Figure 12:
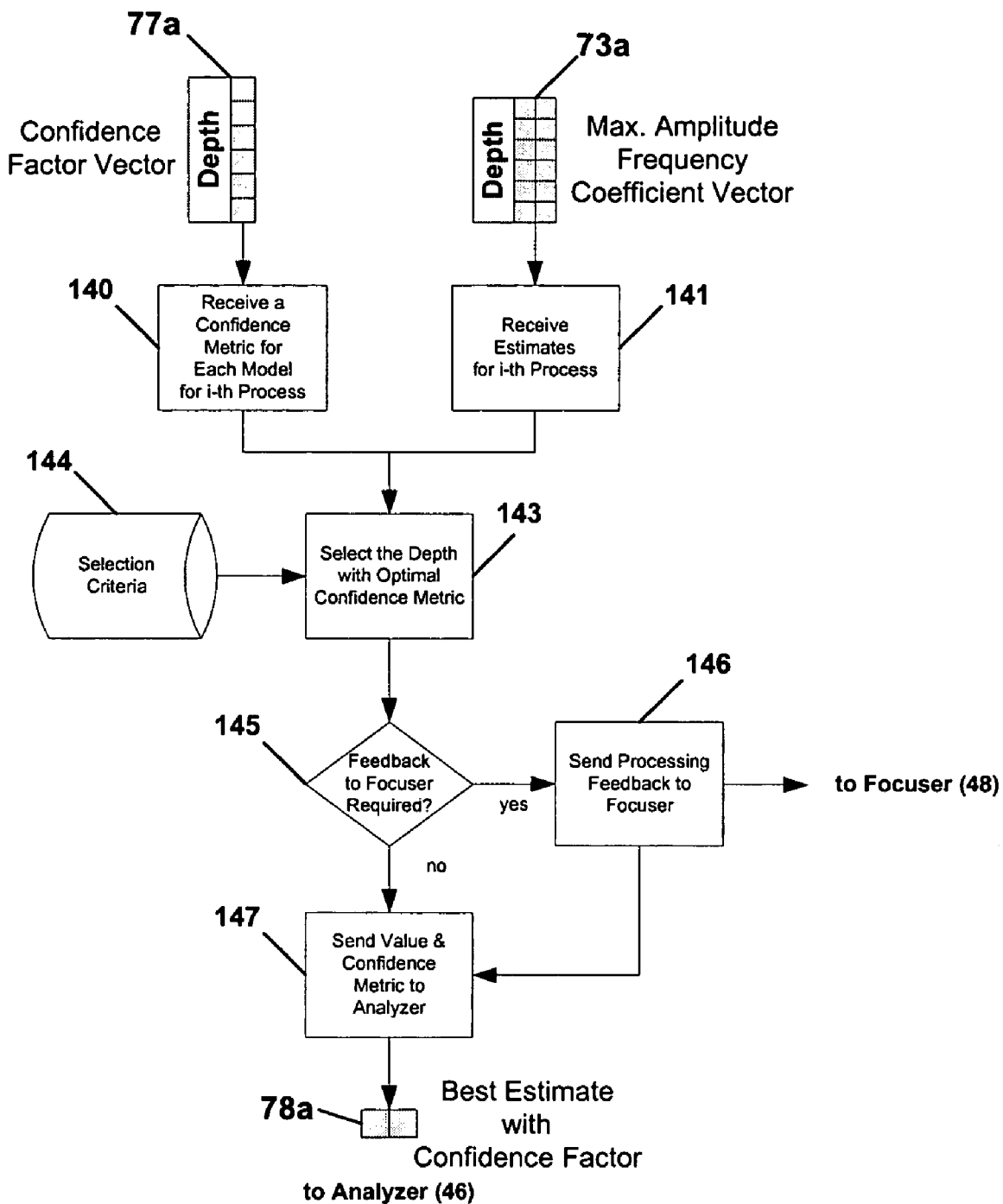
FIG. 12 illustrates a flow chart of the selector and selector signal processing useful in an embodiment of our invention.

A flow chart for the steps involved in the Selector is shown in FIG. 12. The physiological measurements are received from the Estimator 73 in block 141 and the corresponding confidence metrics are received from the Correlator 77 in block 140. Given these two 1×N vectors, the depth with the optimal measurement is selected in block 143 based on the selection criteria in block 144. Decision block 145 determines if the results of the algorithm should be forwarded to the Focuser 48 so that it can modify the system's operation. If this is the case, the information is sent to the Focuser via block 146. In any case, the selected physiological measurement and its corresponding confidence metric are sent to the Analyzer 46 in block 147. These steps are run on each invocation of the Selector for each physiological process being measured.

Corresponding minimum and maximum thresholds on Error E: $(E_L, E_H)$

Alarm if "Mx $\notin (M_L, M_H)$" OR "Ex $\notin (E_L, E_H)$"

Additionally, time series analysis can be extended to calculation of higher order error terms where one or more past error terms are used to create a prediction of future error terms. Calculation of higher order error terms provides more detail on variations in the process under investigation and may allow earlier detection of adverse events. For example, the second order error term can be derived by applying a "moving average filter of degree P" to the series of first order error terms to obtain a prediction of the next first order error term. The difference between the prediction and the actual value is the second order error term.

A third analysis mechanism to detect a problematic trend is to match the sequence of values with a known problematic pattern through correlation. This is accomplished by cross-correlating the time-ordered sequence with a known pattern. For example, for a given sequence of cardiac rate measurements, the sequence could be cross-correlated against patterns for bradycardia, tachycardia, and fibrillation to determine if one of these conditions is occurring or developing.

Figure 13:
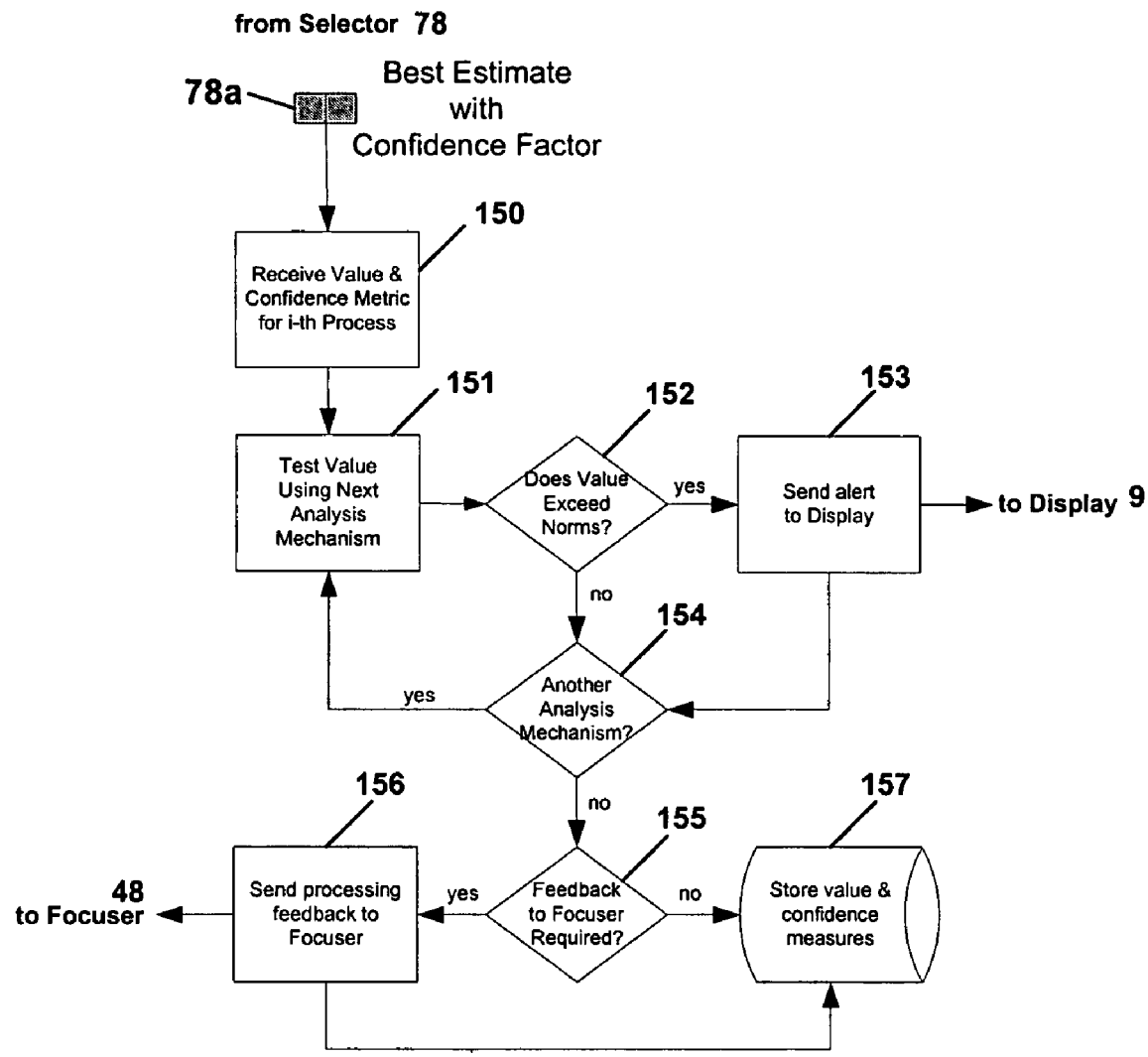
FIG. 13 illustrates a flow chart of the analyzer and analyzer signal processing useful in an embodiment of our invention.

The steps involved in the Analyzer are shown in flow chart in FIG. 13. The optimal value-confidence pair for the current invocation of the algorithm is received from the Selector 78 in block 150. The Analyzer may have several mechanisms to determine if an abnormal trend is developing. In block 151, each mechanism is used to check the stream of data. Decision block 152 determines if the current mechanism has detected a problematic trend. If it has, an alert is sent to the system's display in block 153. In any case, decision block 154 determines if there is another mechanism to try. Mechanisms will continue to be tried even after an alert so that performance statistics can be collected on each analysis mechanism. When all of the analysis mechanisms have been performed, block 155 determines if feedback should be sent to the Focuser 48. If so, it is sent in block 156. In any case, the value-confidence pair is stored in block 157 so that it can be used in the future for detecting trends. These steps are run for each physiological process being measured.

If the Selector explained with respect to FIG. 12 is producing multiple value-confidence pairs because more than one physiological process is being analyzed simultaneously, the Analyzer may process each stream independently and may also use the values from each stream to assist in the analysis of the other stream. For example, in a system designed to measure cardiac and pulmonary rates, the Analyzer would analyze the cardiac and pulmonary streams independently looking for trends, but could also compare the two streams because, for instance, increases in cardiac rate resulting from exertion should, normally, correspond to increases in pulmonary rate.

Focuser

Figure 14:
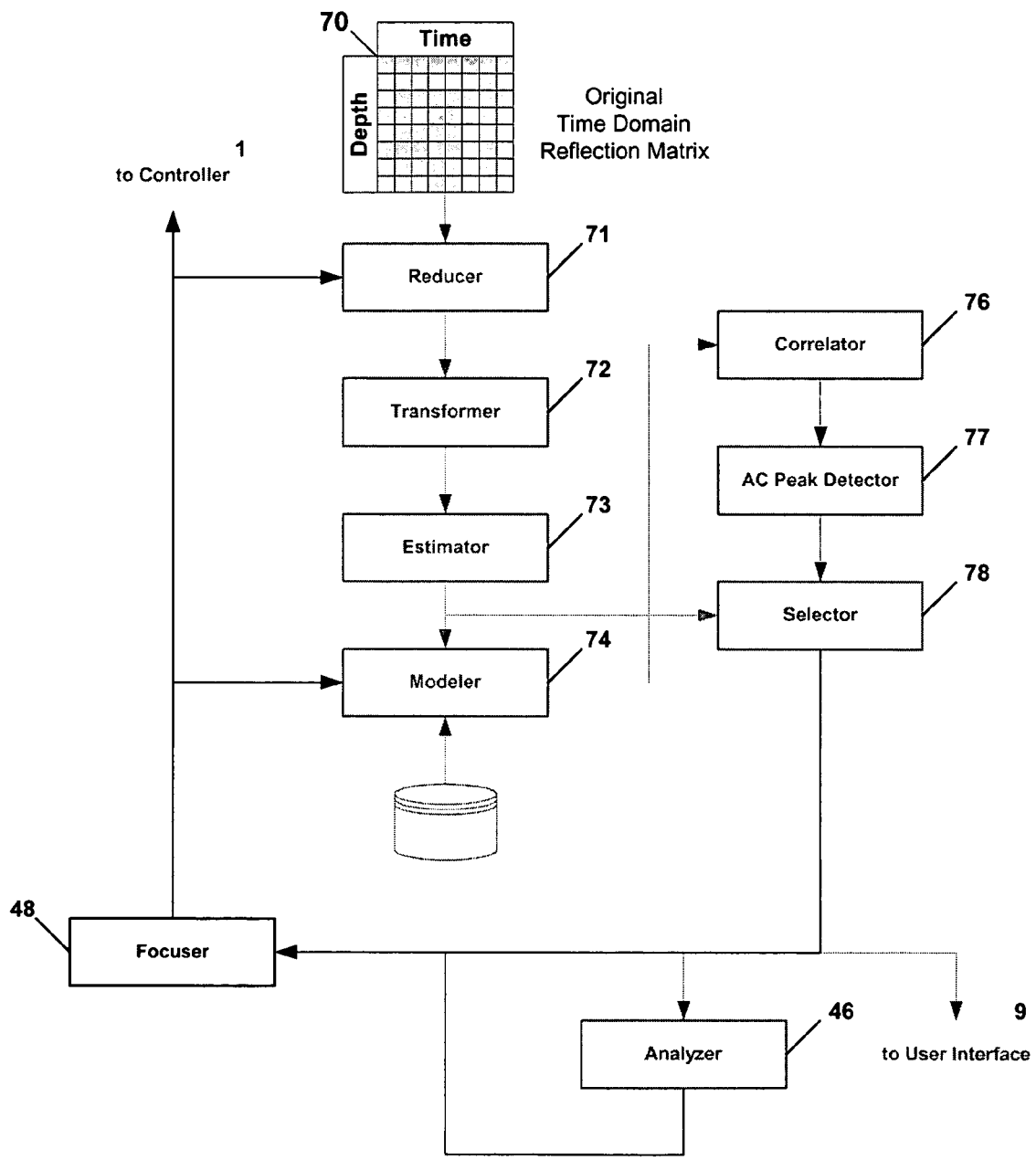
FIG. 14 illustrates a focuser feedback mechanism, and its operation, useful in an embodiment of our invention.

The Focuser 48 of FIG. 4 is a control process that uses the results from one or more of the device's stages to modify the amount and types of processing performed on each pass through the system. It takes inputs from the Extractor's Selector 78 of FIG. 6, and the Analyzer 46 of FIG. 4 and, based on the values received and its internal decision algorithm, modifies the behavior of the Receiver 6 of FIG. 1 and the Extractor 44 of FIG. 4. The Focuser feedback mechanism is illustrated in FIG. 14.

The Focuser may increase, decrease or simply modify the amount of computation done by the system on each iteration. For example, if the trend being analyzed by the Analyzer is extremely stable, the Focuser may decrease the amount of computation to conserve power or resources. If, on the other hand, a problematic trend appears to be developing, it may increase the level of computation.

One scheme to do this is to change the number of depths at which data is processed. That is, the reflections from some depths may be ignored. For example, for a system designed to measure cardiac rate, only the depths near the heart may be processed if the trend is stable and measurements strong. This concept is illustrated in the time domain reflection matrix of FIG. 15. The matrix in FIG. 15 can hold reflection values from m different depths in the body. However, the Focuser has determined that only three depths are worthy of computation. They are termed the "Depth Range of Interest" (shaded area 170) and only the data in those depths will be processed. The remaining data (shaded areas 171, 172) will be ignored.

Figure 15:
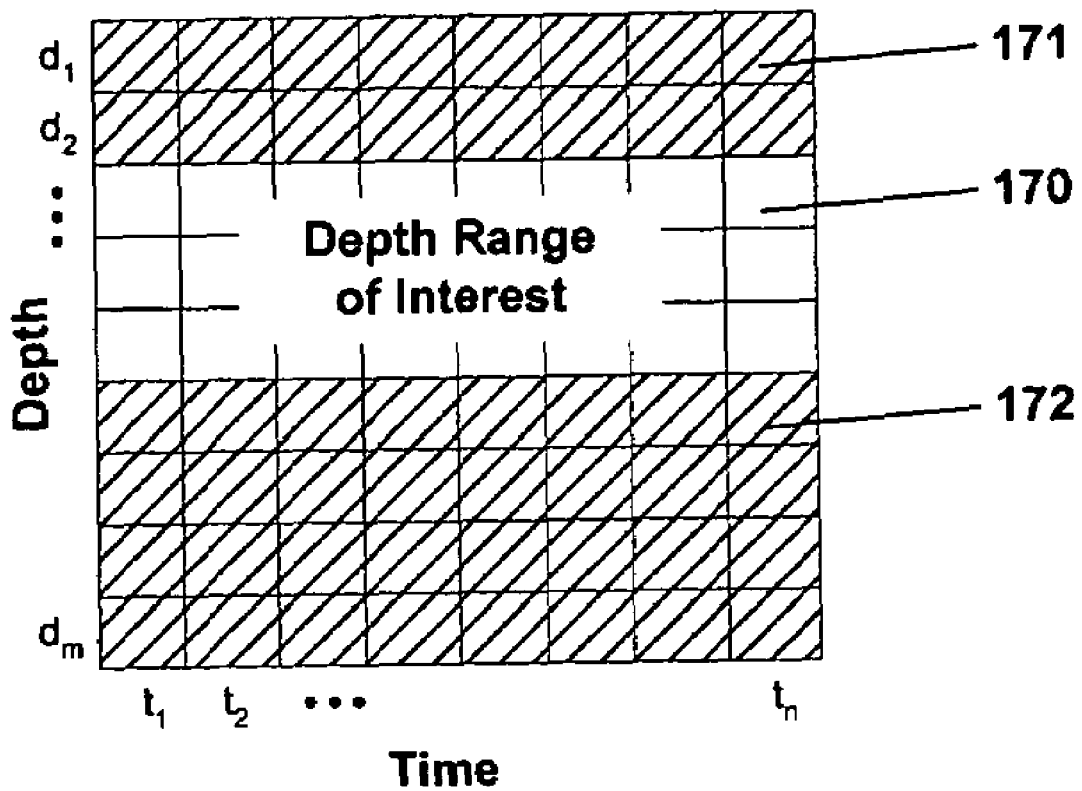
FIG. 15 illustrates a time domain return signal matrix with the depth range of interest highlighted.
Figure 16:
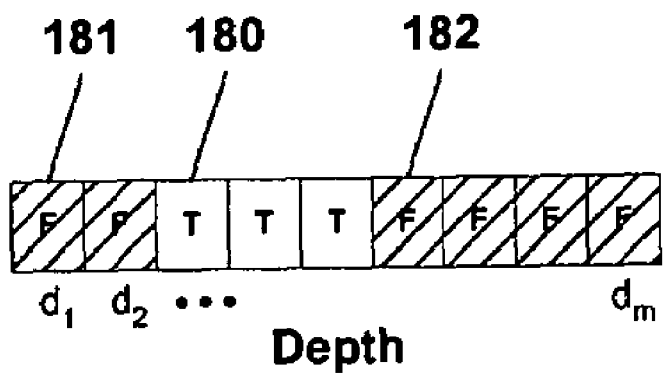
FIG. 16 is a sample depth range of interest indicator useful in an embodiment of our invention.

This depth-focusing process is accomplished by having the Extractor 46 take a Depth Range of Interest (DROI) indicator. It will then only process those entries in the reflections matrix that are in the DROI. The DROI indicator is a 1-dimensional matrix of Boolean values where entry i indicates whether or not the Extractor should process data from depth i. The DROI indicator for the sample time domain reflection matrix in FIG. 15 is illustrated in FIG. 16. The depths that are in the DROI have a "true" value in their cell of the DROI. All other depths have a "false" value.

An alternative focusing scheme is to vary the amount of processing that is done for each depth on each pass through the system. For example, the frequency data may be correlated with only one model to conserve resources or with many models when the system needs to hunt broadly for the best-fit model.

PREFERRED EMBODIMENT EXAMPLE

An Algorithm for Measuring Cardiac Rate

Figure 17:
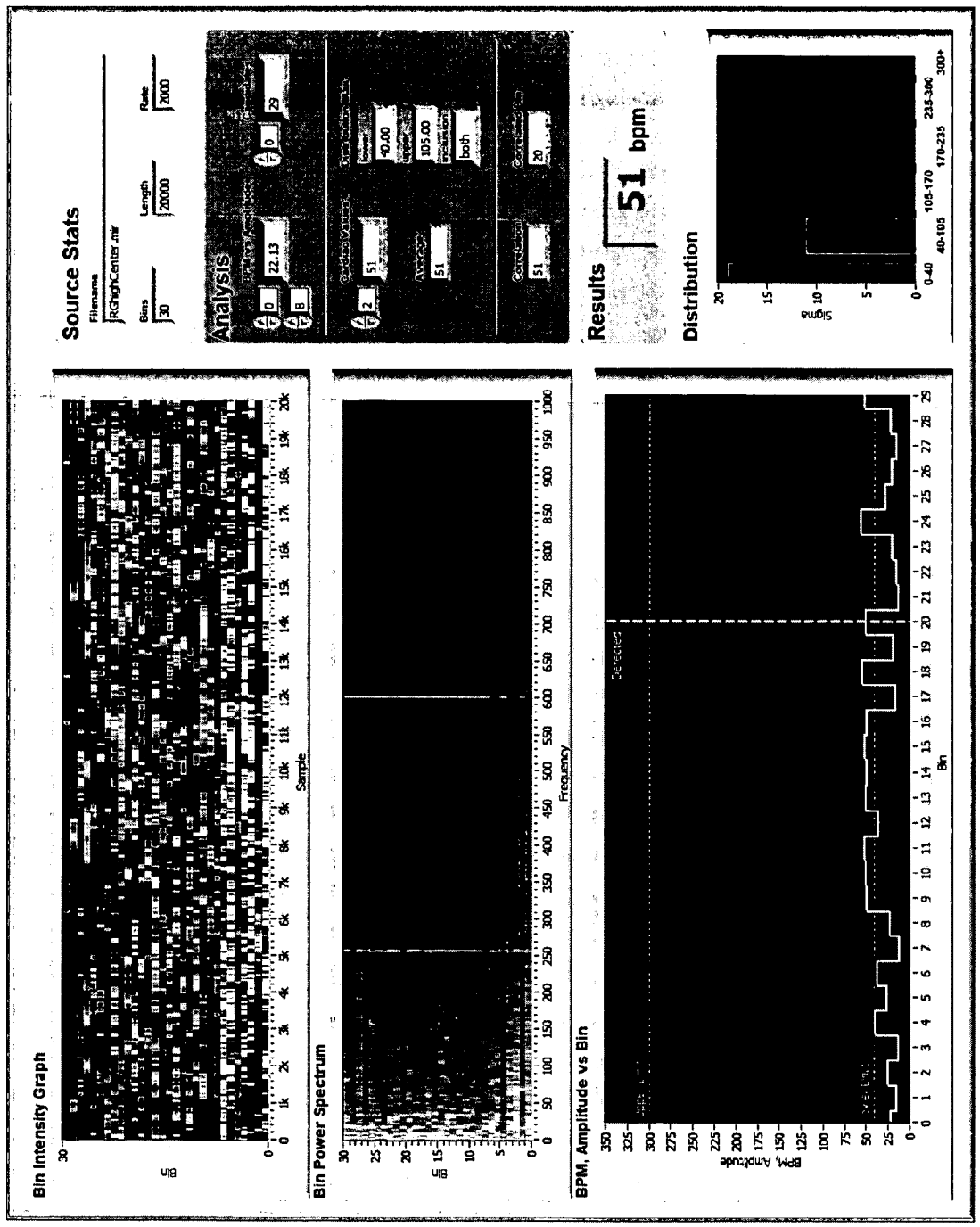
FIG. 17 is a screen shot of an application screen showing part of a graphical user interface useful in one embodiment of our invention.

The user interface for the cardiac rate algorithm is shown in FIG. 17. It illustrates the signals displayed as a result of various intermediate and final calculations associated with the algorithm. The term "bin" is used extensively in the user interface. It is a common term from the study of radar and is synonymous with depth used previously.

Bin Intensity Graph—The two-dimensional graph displays the time-domain reflections acquired at varying depths from the chest surface to the back in a human body. Depth is represented on the vertical axis, number of samples on the horizontal axis, and amplitude (or reflection strength) mapped as a color intensity ranging from black to white across a blue spectrum (white is the greatest signal strength). This graph shows 20,000 samples per depth, which translates to 10 seconds of data at each depth. For operation in range gate mode, the samples must be collected over a time period that is greater than the slowest expected physiological cycle period.

Bin Power Spectrum—After the time-domain data has been processed through a Fast Fourier Transform, the frequency domain results are shown in this two-dimensional graph. Depth is represented on the vertical axis, frequency on the horizontal axis, and amplitude mapped as a color intensity ranging from black to white across a blue spectrum. In this graph, amplitude refers to the strength of the corresponding frequency component in the time-domain data. The discrete vertical lines are thought to be due to 60 cycle noise and system clocks.

BPM, Amplitude vs. Bin—The two-dimensional graph displays both the frequency (green trace) and amplitude (magenta blocks) of the "primary tone" per depth (or bin). The primary tone is the frequency with the greatest amplitude coefficient in each bin. The depth is represented on the horizontal axis with the frequency and amplitude on the vertical axis. In addition, the light brown vertical dotted line labeled "Detected" shows the bin that algorithm has selected as the cardiac location. The selected bin is the one with the highest correlation between the frequency data and the cardiac waveform model. The blue dashed upper and lower limits show the range in which cardiac data is valid (i.e., 40 to 300 beats per minute). Frequencies outside those bounds are ignored.

Source Statistics—This panel displays the current data file name along with its attributes: number of bins, number of samples per bin, and sample rate in hertz.

Results—This panel displays the final cardiac rate in beats per minute as determined by the algorithm.

Distribution—The two dimensional graph displays the distribution of primary tones for cardiac data for the various depths. For example, the graph shows that there were approximately 19 depths that had primary tones between 0 and 40, and approximately 10 depths that had primary tones between 40 and 105.

While the foregoing has been with reference to particular embodiments of the invention, it will be appreciated by those skilled in the art that changes in these embodiments may be made without departing from the principles and spirit of the invention, the scope of which is defined by the appended claims.

We claim:

1. A process employing ultra wideband radar return signals to extract physiological data from one or more bodily organs or physiological processes of a patient, said process comprising:
   generating a baseband pulse train;
   transmitting an emitted signal from a first antenna as an ultra-wide band spectrum signal, wherein the emitted signal comprises a series of low voltage, short-duration pulses triggered by the baseband pulse train;
   outputting a delayed version of the baseband pulse train from a delay range comprising an electronically controlled range gate;
   receiving reflections of the emitted signal at a receiver connected to a second antenna, wherein the receiver is triggered by the delayed version of the baseband pulse train;
   processing the reflections received by the receiver to generate a first matrix of time-sampled reflection values at various depths;
   converting the first matrix of time-sampled reflection values into a second matrix and extracting physiological data from the second matrix using frequency spectrum analysis and statistical filtering.

2. The process of claim 1 wherein the step of outputting a delayed version of the baseband pulse train comprises outputting a delayed version of the baseband pulse train in range gate mode, wherein the delayed version of the baseband pulse train is configured to trigger the receiver to collect reflections at one or more of a subset of said depths.

3. The process of claim 1 wherein the step of outputting a delayed version of the baseband pulse train comprises outputting a delayed version of the baseband pulse train in range finder mode, wherein the delayed version of the baseband pulse train is configured to trigger the receiver to collect reflections across a range of said depths.

4. The process of claim 1 further comprising operating on said second matrix to suppress certain high-strength reflection signals and amplify signals representing motion within said patient.

5. The process of claim 1, wherein the processing step includes low-pass filtering, said low pass filtering passing frequencies up to 5 Hz, and minimizing the potential of aliasing prior to generating the first matrix of time-sampled reflection values.

6. The process of claim 1, wherein the processing step includes low-pass filtering, said low pass filtering passing frequencies up to 200 Hz, and minimizing the potential of aliasing prior to generating the first matrix of time-sampled reflection values.

7. The process of claim 1, further comprising digitizing the reflections of the emitted signal received by the receiver from analog to digital into a series of discrete numerical values representing the amplitudes of said reflections of the emitted signal.

8. The process of claim 4, wherein the first matrix is a two-dimensional matrix of time-sampled reflection values from various depths.

9. The process of claim 8 wherein the two-dimensional matrix stores a matrix of reflections of the emitted signal at various depths and times.

10. The process of claim 8 wherein the depth of said various depths within the patient from which said time-sampled reflection values are collected is fixed and a number of samples of said time-sampled reflection values are collected at said fixed depth over a period of time.

11. The process of claim 8 wherein the depth of said various depths within the patient from which time-sampled reflection values are collected is varied over a finite range of said depths of interest and samples of said time-sampled reflection values are collected at a plurality of said depths.

12. The process of claim 1, wherein the step of converting the first matrix of time-sampled reflections values into a second matrix comprises reducing data from said first matrix.

13. The process of claim 12 wherein said reducing includes the step of averaging values of said time-sampled reflection values to reduce the volume of time-sampled data.

14. The process of claim 1, wherein the converting step includes the step of coarse quantizing to increase contrast and reduce computational complexity of said time-sampled reflection values.

15. The process of claim 1, wherein the converting step includes the step of normalizing to maximize the dynamic range of said time-sampled reflection values.

16. An ultra wideband sensor device for extracting physiological data from a patient, said device comprising:
   a pulse repetition frequency generator configured to generate a baseband pulse train;
   a transmitter connected to a first antenna, the transmitter configured to generate a series of low voltage, short-duration pulses based on the baseband pulse train for transmission as an emitted signal from the first antenna as an ultra-wide band spectrum signal;
   a delay range configured to output a delayed version of the baseband pulse train;
   a receiver connected to a second antenna, the receiver triggered by the output of the delay range wherein the receiver is configured to process reflections of the emitted signal received by the second antenna;
   a controller configured to emit a synchronization signal; and
   a signal processor including an extractor, wherein the signal process is configured to process information from the receiver and to generate a first matrix of time-sampled reflection values at various depths and sample intervals of the synchronization signal, and wherein the extractor is configured to optimize the information in the first matrix to derive a second matrix from which physiological data may be extracted,
   wherein the controller synchronizes the activity of the transmitter and signal processor.

17. The device of claim 16, further comprising a user interface for displaying the extracted physiological data.

18. The device of claim 16 wherein the delay range is configured to operate in a range gate mode and a range finder mode.

19. The device of claim 16 wherein the extractor is configured to indicate a cardiopulmonary measurement.

20. The device of claim 16 wherein the signal processor comprises a focuser configured to modify the processing of information from the receiver based on information extracted from past time-sampled reflection data.

21. The device of claim 16 wherein the signal processor comprises a reducer configured to process the first matrix of time-sampled reflection data and output a modified matrix of time-sampled reflection data.

22. The device of claim 21 wherein the reducer is configured to subtract static reflections from the first matrix of time-sampled reflection data to generate the modified matrix of time-sampled reflection data.

23. The device of claim 21 wherein the reducer is configured to reduce the size of the first matrix of time-sampled reflection data in creating the modified matrix of time-sampled reflection data.

24. The device of claim 21 wherein the reducer is configured to normalize the values of the first matrix of time-sampled reflection data to generate the modified matrix of time-sampled reflection data.

25. The device of claim 16 wherein the signal processor comprises a transformer configured to transform the first matrix of time-sampled reflection data to the frequency domain.

26. The device of claim 16 wherein the signal processor comprises a transformer configured to transform the second matrix of time-sampled reflection values to the frequency domain.

27. The device of claim 16 wherein the signal processor comprises an estimator configured to estimate physiological parameter from the amplitudes of values from the second matrix of time-sampled reflection data.

28. The device of claim 16 wherein the signal processor comprises:
   a modeler including a database of filters for matching against the reflection values in the second matrix; and
   a correlator to calculate a matrix of correlation coefficients based on the correlation of the reflection values in the second matrix and one or more of the filters in the database.

29. The device of claim 16 wherein the signal processor comprises a selector configured to process a confidence value of the indicator of a physiological measurement of the patient.

30. The device of claim 16, further comprising an analyzer configured to detect deviation of the indicator of physiological measurement output by the signal processor from one or more expected ranges.

31. The device of claim 16 wherein the transmitter is immediately adjacent to the antenna and the receiver is immediately adjacent to either the antenna or a second antenna.

32. The device of claim 16 wherein the ultra wideband receiver comprises a second antenna.

33. A process employing ultra wideband radar return signals to extract physiological data from one or more bodily organs or physiological processes of a patient, said process comprising:
   transmitting an emitted signal from an antenna as an ultra-wide band spectrum signal, wherein the emitted signal comprises a plurality of individual low voltage, short-duration pulses;
   receiving a plurality of reflections for each individual low voltage, short-duration pulses of the emitted signal at a receiver, wherein each reflection corresponds to a depth into the patient's body based on a fixed time-delay from the emitted signal;
   processing the reflections received by the receiver to generate a first matrix of time-sampled reflection values at a plurality of depths for at least a subset of the plurality of individual low voltage, short-duration pulses;
   converting the first matrix of time-sampled reflection values into a reduced matrix; and
   extracting physiological data from the reduced matrix using frequency spectrum analysis and statistical filtering.

34. An ultra wideband sensor device for extracting physiological data from a patient, said device comprising:
   a pulse repetition frequency generator configured to generate a baseband pulse train;
   a transmitter connected to an antenna, the transmitter configured to generate a series of low voltage, short-duration pulses triggered by the baseband pulse train for transmission as an emitted signal from the antenna as an ultra-wide band spectrum signal;
   a delay range configured to output a delayed version of the baseband pulse train;
   an ultra wideband receiver, the receiver triggered by the output of the delay range to detect reflections of the emitted signal at different depths; and
   a signal processor configured to process reflections of the emitted signal received by the receiver and to generate a first matrix of time-sampled reflection values at various depths and time intervals, wherein the signal processor includes an extractor that is configured to optimize the information in the first matrix to derive a second matrix from which physiological data may be extracted.

35. The device of claim 34, further comprising a controller configured to emit a synchronization signal to synchronize the operation of the transmitter and signal processor.

36. The device of claim 34, further comprising a user interface for displaying the extracted physiological data.

37. The device of claim 34 wherein the delay range is configured to operate in a range gate mode and a range finder mode.

38. The device of claim 34 wherein the extractor is configured to indicate a cardiopulmonary measurement.

39. The device of claim 34 wherein the signal processor comprises a focuser configured to modify the first matrix of time-sampled reflection values based on information extracted from past time-sampled reflection data.

40. The device of claim 34 wherein the signal processor comprises a reducer configured to process the first matrix of time-sampled reflection values and output a modified matrix of time-sampled reflection data.

41. The device of claim 40 wherein the reducer is configured to subtract static reflections from the first matrix of time-sampled reflection values to generate the modified matrix of time-sampled reflection data.

42. The device of claim 40 wherein the reducer is configured to reduce the size of the matrix of time-sampled reflection values in creating the modified matrix of time-sampled reflection data.

43. The device of claim 40 wherein the reducer is configured to normalize the values in the matrix of time-sampled reflection values to generate the modified matrix of time-sampled reflection data.

44. The device of claim 40, wherein the ultra wideband receiver comprises a second antenna.

45. The device of claim 34 wherein the signal processor comprises a transformer configured to transform the first matrix of time-sampled reflection values to the frequency domain.

46. The device of claim 34 wherein the signal processor comprises a transformer configured to transform the second matrix of time-sampled reflection values to the frequency domain.

47. The device of claim 34 wherein the signal processor comprises an estimator configured to estimate physiological parameter from the amplitudes of values from the second matrix of time-sampled reflection data.

48. The device of claim 34 wherein the signal processor comprises:
   a modeler including a database of filters for matching against the reflection values in the second matrix; and a correlator to calculate a matrix of correlation coefficients based on the correlation of the reflection values in the second matrix and one or more of the filters in the database.

49. The device of claim 34 wherein the signal processor comprises a selector configured to process a confidence value of the indicator of a physiological measurement of the patient.

50. The device of claim 34, further comprising an analyzer configured to detect deviation of the indicator of physiological measurement output by the signal processor from one or more expected ranges.

51. The device of claim 34, wherein the transmitter is immediately adjacent to the antenna.

* * * * *